United States Patent [19]

De Luca et al.

[11] Patent Number: 4,808,728

[45] Date of Patent: Feb. 28, 1989

[54] PRODUCTION OF INDOLEPYRUVIC ACID AND THE 5-HYDROXY DERIVATIVE THEREOF

[75] Inventors: Giovanna De Luca; Giovanni Di Stazio; Andrea Margonelli; Mario Materazzi; Vincenzo Politi, all of Rome, Italy

[73] Assignee: Polifarma S.p.A., Rome, Italy

[21] Appl. No.: 33,099

[22] PCT Filed: Jun. 24, 1986

[86] PCT No.: PCT/IT86/00045

§ 371 Date: Mar. 2, 1987

§ 102(e) Date: Mar. 2, 1987

[87] PCT Pub. No.: WO87/00169

PCT Pub. Date: Jan. 15, 1987

[30] Foreign Application Priority Data

Jun. 28, 1985 [IT] Italy .............................. 48295 A/85

[51] Int. Cl.$^4$ .......................................... C07D 209/18
[52] U.S. Cl. .................... 548/502; 548/497
[58] Field of Search .............................. 548/502, 494

[56] References Cited

U.S. PATENT DOCUMENTS 4,551,471 11/1985 De Luca .............................. 548/497

FOREIGN PATENT DOCUMENTS 0106813 4/1984 European Pat. Off. .

OTHER PUBLICATIONS

Sidgwick, The Org. Chem. of Nitrogen (1937) Clarendon Press Oxford (p. 104).
Chem. Abstracts, vol. 73, No. 17, 26 Oct. 1970 (Columbus, OH), T.-T. Kuo et al: "Role of Aminotransferase and Indole-3-Pyruvic Acid in the Synthesis of Indole-3-Acetic Acid in Pseudomonas Savas-Tanoi", pp. 36-37.
Chem. Abstracts, vol. 69, No. 21, 18 Nov. 1968 (Columbus, OH), T. C. Moore et al.: "Synthesis of Indoleacetic Acid from Trypotophan via Indolepyruvic Acid in Cell-Free Extracts of Pea Seedlings", p. 7860.

Primary Examiner—David B. Springer
Attorney, Agent, or Firm—Cushman, Darby & Cushman

[57] ABSTRACT

Tryptophan and esters thereof, and other indoleaminoacids, can be easily transformed into respective alpha-ketoacids through a coupling reaction with aromatic aldehydes, in the presence of a dehydrating agent.

8 Claims, No Drawings

PRODUCTION OF INDOLEPYRUVIC ACID AND THE 5-HYDROXY DERIVATIVE THEREOF

DESCRIPTION

The present invention relates to a process for synthetically producing alpha-ketoacids from their respective alpha-aminoacids.

This invention is particularly useful for the production of 3-indolepyruvic acid and the derivatives thereof, from tryptophan.

Various methods for the synthesis of 3-indolepyruvic acid have been described in the literature.

Ellinger and Matsouka (Hoppe-Seylers z.109, 259 (1920)) obtained the ketoacid by condensation of indole-3-aldehyde and benzoyl-glycine, followed by hydrolysis of the reaction product (2-phenyl-4-indolyl-methylene-5-oxazolone).

Bentley et al (Biochem. J. 64, 44 (1956)) had instead condensed indole-3-aldehyde with hydantoin, followed by acidification with sulphuric acid.

Kaper et al (Arch. Bioch, Biophys. 103, 469 (1963)), after the condensation reaction of indole-3-aldehyde with hydantoin, reacted the compound thus obtained with barium hydroxide, followed by acidification with hydrochloric acid.

Sakurai (J. Biochem. 44, 47 (1957)) used methyl-indoleacetate as a starting material in a reaction with diethyloxalate.

In U.S. Pat. No. 4,551,471 a synthesis of 3-indolepyruvic acid is described starting from L-tryptophan, under the action of the enzyme aspartate-aminotransferase, obtained from mitochondria of animal organs.

It has now been found, and this is the object of the present invention, that tryptophan, both in the form of the individual L- and D-isomers, and the D,L-mixture, can be used as a starting compound for a chemical synthesis of 3-indolepyruvic acid with high yields.

The process according to the invention, however, can be used in a general way to obtain indole-alpha-ketoacids from their respective D,L-alpha-aminoacids and an aromatic aldehyde.

Object of the present invention is thus a process for the production of indole-alpha-ketoacids through a coupling reaction of an indole-alpha-aminoacid or an ester thereof, and an aromatic aldehyde, wherein said reaction is carried out in the presence of a basic dehydrating proton acceptor agent in a solvent which can be anhydrous.

Consequently the invention is characterized by the use of an agent having a high dehydrating power with respect to a coupling reaction, which reaction is assumed to lead to a Schiff base.

According to the invention, particularly preferred as a dehydrating agent are 1,8-diazabicyclo(5.4.0)-undec-7-ene, hereafter indicated by the abbreviation DBU, and also a salt containing a metal which can form a stable bond with the reaction intermediates. Particularly preferred among said salts is zinc chloride which is assumed to form a complex with the intermediate of synthesis. DBU is a reactant which has been used so far for completely different processes, such as the insertion of silane groups into organic compounds (Tetrahedron Lett. 26, 475, 1985), the esterification of carboxylic acids (Bull. Chem. Soc. Jap. 51, 2401, 1978) or the preparation of peptides (Tetrahedron 40, 4237, 1984). There is no indication in the literature of a use of DBU as provided in the present invention.

As aldehydes to be reacted with the alpha-aminoacid, aromatic aldehydes are preferred.

Representatives of said aldehydes are isonicotinaldehyde and hydroxy derivatives of benzaldehyde, which are particularly preferred.

The solvent used in the reaction can be an anhydrous solvent. Representatives thereof are dimethylformamide (DMF) and acetonitrile. A aqueous solvent can also be used. Representatives of this are DMF and methanol.

The reaction can be carried out at room temperature with good results, depending anyway on the particular species of aminoacids to be reacted.

The process of the present invention has shown itself particularly effective for the production of 3-indolepyruvic acid, in that the reaction runs with very high yields (higher than 50%) with respect to the tryptophan or its ester. However, as stated above, the process is of more general validity, as tryptophan which is substituted in 5-position has also shown to react under the same conditions.

Examples of preparation of the process according to the invention are illustrated hereinafter.

EXAMPLE 1

Preparation of indolepyruvic acid from tryptophan

A suspension of 0,658 g tryptophan in 10 ml dimethylformamide (DMF) rendered anhydrous by passage on molecular sieves or on neutral alumina column and under dry nitrogen atmosphere, is quickly added with 0,688 ml isonicotinaldehyde. An almost complete solubilization of the suspension occurs with a colour tending towards yellow. The system is cooled with an ice bath and it is immediately slowly added with 1,0 ml of 1,8-diazabicyclo(5.4.0)-undec-7-ene (DBU), previously dissolved in 5 ml DMF rendered anhydrous as above indicated.

The solution changes from yellow to blood red.

The reaction mixture is brought to room temperature and maintained under stirring and dry nitrogen for one night.

The mixture is poured into a double volume of previously cooled HCl 1,0N, the system being kept under stirring for 15 minutes. It is extracted by ethyl acetate (5×25 ml). The organic phase is washed successively with HCl 0,1N, then with a saturated NaCl solution. The organic phase is dried on anhydrous $Na_2SO_4$ for one night. It is filtered, the organic solvent is evaporated and after purification 329 mg indolepyruvic acid are obtained with a 50% yield with respect to the initial tryptophan.

Analysis NMR, IR and melting point of the indolepyruvic acid conform to the data of literature.

EXAMPLE 2

Preparation of indolepyruvic acid from tryptophan methylester hydrochloride

To 10 ml DMF or acetonitrile ($CH_3CN$), which has been rendered anhydrous by passage on molecular sieves or neutral alumina column, 300 mg tryptophan methylester hydrochloride and successively 0,170 ml triethylamine are added under dry nitrogen atmosphere, the system being kept under stirring for 30 minutes at room temperature. Again under dry nitrogen atmosphere 0,280 ml isonicotinaldehyde are quickly added under stirring and a pale yellow solution is obtained.

Then 0,5 ml DBU dissolved in anhydrous DMF solution is slowly added. The reaction mixture changes from yellow to blood red.

The system is maintained under stirring and dry nitrogen atmosphere for one night. At the end of this time the mixture is poured into a double volume of HCl 1N and heated to 60° under stirring. The reaction mixture is cooled and extracted with ethylacetate (5×15 ml). The organic phase is successively washed with HCl 0,1N and a saturated NaCl solution. The organic phase is dried on $Na_2SO_4$ for one night. It is filtered, the organic solvent is evaporated and after purification 155 mg indolepyruvic acid are obtained in 65% yield with respect to initial tryptophan-methylester HCl.

The NMR, IR analysis and the melting point of indolepyruvic acid conform to the data of literature.

EXAMPLE 3

Preparation of indolepyruvic acid from tryptophan methylester hydrochloride

Example 2 is followed until obtaining the pale yellow solution. At this point, before adding DBU, 96 mg anhydrous $ZnCl_2$ are slowly added under stirring. The reaction mixture changes from yellow to blood red.

By operating as described in example 2, 155 mg of indolepyruvic acid are obtained in a 65% yield with respect to the initial tryptophan methylester hydrochloride.

EXAMPLE 4

Preparation of indolepyruvic acid from L- or D,L-tryptophan in methanol 34 ml methanol are additioned at room temperature (about 20° C.) with 5 g tryptophan and, under stirring, 4 ml triethylamine (TEA) are added.

After 10 minutes, 3,98 ml of isonicotinaldehyde (ISNA) are quickly added under stirring. The solution changes from milk white to greenish gold yellow.

Stirring is continued for additional 15 to 20 minutes. Then 2,0 g $ZnCl_2$ are quickly added and a full yellow precipitate is obtained. It is stirred vigorously for additional 10 minutes and 8,07 DBU previously dissolved in 6 ml methanol are quickly added dropwise. The additions are made in about 5 minutes. An orange red solution is eventually obtained which tends very quickly to darken, while a slow dissolution of the precipitate occurs.

After about 80 to 90 minutes from the last addition, the dark red mixture devoid of the precipitate is added rapidly dropwise under vigorous stirring into about 300 ml HCl 1N previously heated to about 55° C. A clear orange solution is obtained.

After about 10 minutes stirring and at about 55° C., a noticeable precipitation of a flocculant yellow solid occurs, which tends to become increasingly thick.

After about 30 minutes, heating is cut off and the mixture is freely allowed to drop to room temperature (about 20° C.) under stirring.

After about 3 hours, a canary yellow solid is suction filtered and repeatedly washed firstly with 20 ml HCl 1M/methanol (10:1), then with cold water to obtain a non-acid and uncoloured filtrate.

This is placed in a vacum dryer for one night. 3,1 g (about 62% yield) indolepyruvic acid are obtained with 100% purity (HPLC, NMR, IR, UV in agreement).

EXAMPLE 5

Preparation of 5-OH indolepyruvic acid (5HIPA)

Following substantially the procedure as described in the examples 1, 2 and 3, 5-OH tryptophan or 5-OH-tryptophan-methylester hydrochloride is transformed into 5-OH-IPA.

The above examples show that the invention is particularly effective in a process for the chemical synthesis of 5-OH-indolepyruvic acid.

We claim:

1. A process for the production of indolepyruvic acid or the 5-hydroxy derivative thereof comprising:
   reacting typtophan or 5-hydroxytryptophan, respectively, or a lower alkyl ester thereof, with a pyridine aldehyde in an essentially anhydrous polar organic solvent in the presence of a tertiary amine base; and
   hydrolyzing the resulting reaction mixture with a strongly acidic aqueous solution to obtain a precipitate consisting essentially of indolepyruvic acid or its 5-hydroxy-derivative, respectively.

2. The process according to claim 1, wherein said polar organic solvent is selected from the group consisting of dimethylformamide, acetonitrile, methanol, and mixtures thereof.

3. The process according to claim 1, wherein said tertiary amine base is selected from the group consisting of 1,8-diazabicyclo(5.4.0)-undec-7-ene, triethylamine, and mixtures thereof.

4. The process according to claim 1, wherein said pyridine aldehyde is isonicotinaldehyde.

5. The process according to claim 1, wherein said reaction is further carried out in the presence of zinc chloride.

6. The process according to claim 1, wherein said polar organic solvent is selected from the group consisting of dimethylformamide, acetonitrile, methanol, and mixtures thereof, and said tertiary amine base is selected from the group consisting of 1,8-diazabicyclo(5.4.0)-undec-7-ene, triethylamine, and mixtures thereof.

7. The process according to claim 1, wherein said polar organic solvent is selected from the group consisting of dimethylformamide, acetonitrile, methanol, and mixtures thereof, and said tertiary amine base is selected from the group consisting of 1,8-diazabicyclo(5.4.0)-undec-7-ene, triethylamine, and mixtures thereof and said pyridine aldehyde is isonicotinaldehyde.

8. A process according to claim 1, wherein said reaction is carried out at room temperature.

* * * * *